(12) United States Patent
Horkay et al.

(10) Patent No.: US 7,380,477 B2
(45) Date of Patent: Jun. 3, 2008

(54) METHOD FOR TISSUE OSMOMETRY

(75) Inventors: Ferenc Horkay, Rockville, MD (US);
Peter Basser, Washington, DC (US);
Adam Berman, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 70 days.

(21) Appl. No.: 11/567,105

(22) Filed: Dec. 5, 2006

(65) Prior Publication Data

US 2007/0113688 A1 May 24, 2007

Related U.S. Application Data

(60) Division of application No. 11/046,199, filed on Jan. 28, 2005, now abandoned, which is a continuation of application No. PCT/US03/24935, filed on Aug. 7, 2003.

(60) Provisional application No. 60/401,935, filed on Aug. 7, 2002.

(51) Int. Cl.
*G01N 5/02* (2006.01)
*G01N 13/04* (2006.01)

(52) U.S. Cl. .......... 73/865; 73/64.47; 73/580; 73/866

(58) Field of Classification Search ........... 73/865.6, 73/866, 580, 865, 64.47
See application file for complete search history.

(56) References Cited

U.S. PATENT DOCUMENTS

| | | | |
|---|---|---|---|
| 4,227,399 A * | 10/1980 | Groninger | 73/73 X |
| 5,134,891 A * | 8/1992 | Canevet et al. | 73/866 |
| 5,235,238 A | 8/1993 | Nomura et al. | |
| 5,685,192 A * | 11/1997 | Shriner et al. | 73/73 |
| 6,007,690 A | 12/1999 | Nelson et al. | |
| 6,020,047 A | 2/2000 | Everhart | |
| 6,251,601 B1 | 6/2001 | Bao et al. | |
| 6,373,169 B1 | 4/2002 | Wajima | |
| 6,515,402 B2 | 2/2003 | Klee et al. | |
| 6,746,708 B2 | 6/2004 | Shen | |
| 6,928,877 B2 * | 8/2005 | Carlson et al. | 73/865.6 X |
| 7,100,428 B1 * | 9/2006 | Dziki | 73/73 |
| 7,171,843 B2 * | 2/2007 | Laswell et al. | 73/38 |
| 7,310,995 B2 * | 12/2007 | Dziki | 73/73 |
| 2005/0269215 A1 | 12/2005 | Horkay et al. | |

OTHER PUBLICATIONS

PCT International Search Report; PCT/US03/24935, Aug. 7, 2003, (Mar. 3, 2004), date mailed), 4 pages.

(Continued)

*Primary Examiner*—Thomas P Noland
(74) *Attorney, Agent, or Firm*—Venable LLP; Michael A. Sartori; Steven J. Schwarz

(57) ABSTRACT

A measurement system including a staging unit including a substrate having piezoelectric properties and a conductive electrode formed on the substrate, the conductive electrode including an area adapted to receive a sample, and an oscillator coupled to the conductive electrode. A method including in a tissue sample having a mass of less than about one microgram and that exerts a high osmotic pressure, calculating an osmotic pressure value for the tissue sample from a plurality of measurements of changes in the mass due to swelling.

7 Claims, 4 Drawing Sheets

OTHER PUBLICATIONS

Horkay, Ferenc, et al., "New tissue micro-osmometer", *225th ACS National Meeting New Orleans*, LA Mar. 23-27, 2003, Biotechnology Divisional, Abstracts, (Mar. 23, 2003), 1 page.

Horkay, Ferenc, et al., "Osmoto investigations on cartilage biopolymers and tissue engineered cartilage samples using a new tissue microosmometer", *Abstract Biophysical Journal*, 86 (1) 480A-480A Part 2 Suppl. S, (2004), 1 page.

Horkey, Ferenc, et al., "Osmotic observations on soft gels and biological tissue samples", *Biochemistry, 42* (28), 249, Laboratory of Integrative and Medical Biophysics, National Institutes of Health, NICHD, Department of Pathology, Washington, Hospital Center,(2003),1 page.

* cited by examiner

METHOD FOR TISSUE OSMOMETRY

CROSS-REFERENCE TO RELATED APPLICATIONS

This application is a divisional application of U.S. patent application Ser. No. 11/046,199, filed Jan. 28, 2005, now abandoned which is a continuation under 35 U.S.C. § 111(a) of PCT/US2003/024935, filed Aug. 7, 2003 and published in English as WO 2004/015376 A2, which claimed priority under 35 U.S.C. § 119(e) and the benefit of the filing date of U.S. provisional application Ser. No. 60/401,935 filed Aug. 7, 2002, which applications and publications are incorporated herein by reference.

STATEMENT OF GOVERNMENT RIGHTS

This invention was developed with the support from the Department of Health and Human Services. The United States Government has certain rights in the invention.

FIELD OF THE INVENTION

This invention relates to measurements and, more particularly, to measurement systems and methods for measuring small quantities of materials.

BACKGROUND OF THE INVENTION

Measurement systems and methods for measuring macroscopic quantities, such as quantities on the order of grams or kilograms, are well developed and readily available. However, as more scientists and engineers examine the microscopic properties of materials, the demand for microscopic and nano-scale measurements increases. This demand for the measurement of small quantities is further driven by the desire of many scientists and engineers to understand material properties that are derived from measurements related to small changes in the mass of materials.

Unfortunately, the measurement of small quantities of materials and changes in small quantities of materials presents difficult problems. Some of the problems result from the fact that many macro-measurement systems do not scale easily to the measurement of nano-scale quantities. For example, mechanical balances used in the measurement of macro-quantities may not be modifiable to provide accurate measurements in the nano-gram range. Additional problems, such as the degradation of samples with the passage of time, arise in the measurement of some samples, such as biological samples. Despite the difficult problems that must be solved to achieve nano-scale measurements, the demand for systems capable of measuring small quantities of materials continues to increase.

SUMMARY OF THE INVENTION

The above mentioned problems related to measurement systems and methods, as well as other problems, are addressed by the present invention and will be understood by reading and studying the following specification.

In one embodiment, a measurement system includes a staging unit including a substrate having piezoelectric properties and a conductive electrode formed on the substrate, the conductive electrode including an area adapted to receive a sample, and an oscillator coupled to the conductive electrode.

In an alternative embodiment, a measurement system includes a staging unit including a substrate having piezoelectric properties and areas of the substrate adapted to receive a sample and a conductive electrode formed on the substrate, and an oscillator coupled to the conductive electrode.

In another alternative embodiment, a measurement system includes an enclosure having a humidity level that is controllable, a staging unit mountable within the enclosure, the staging unit including a substrate having piezoelectric properties, a conductive electrode formed on the substrate and a monolayer formed on the conductive electrode and adapted to receive a sample, and a variable oscillator coupled to the conductive electrode.

In yet another alternative embodiment, a measurement system includes a staging unit including a substrate having piezoelectric properties, and a conductive electrode formed on the substrate, the conductive electrode adapted to receive a tissue sample.

In still another alternative embodiment, a staging unit includes a substrate having piezoelectric properties, a conductive electrode formed on the substrate, and a monolayer formed on the conductive electrode and adapted to receive a sample.

In one embodiment, a method includes in a tissue sample having a mass of less than about one microgram, measuring changes on the order of about one nanogram in the mass due to swelling.

In an alternative embodiment, a method includes in a tissue sample having a mass of less than about one microgram and that exerts a high osmotic pressure, calculating an osmotic pressure value for the tissue sample from a plurality of measurements of changes in the mass due to swelling.

In another alternative embodiment, a method includes attaching a sample having a mass to a conductive electrode formed on a substrate, serially placing the substrate in a plurality of enclosures, each of the plurality of enclosures having a different humidity level and measuring the mass of the sample in each of the plurality of enclosures to form a plurality of measurement values.

In yet another alternative embodiment, a method includes attaching a polyvinylalcohol hydrogel including a sample having a mass to a conductive electrode formed on a substrate, the polyvinylalcohol hydrogel to improve adhesion or attachment between a substrate and the sample, serially placing the substrate in a plurality of closed containers, each of the plurality of closed containers having a different humidity level, measuring the mass of the sample in each of the plurality of closed containers to form a plurality of measurement values, and calculating an osmotic pressure value for the sample from the plurality of measurement values.

In still another alternative embodiment, a method includes identifying a resonant frequency of a substrate having a conductive electrode formed thereon, attaching a gel-like sample having a mass to the conductive electrode, measuring a second resonant frequency of the substrate with the sample attached to the substrate and calculating the mass of the sample.

These and other embodiments, aspects, advantages and features of the present invention will be set forth in part in the description which follows, and in part will become apparent to those skilled in the art by reference to the following description of the invention and referenced drawings or by practice of the invention. The aspects, advantages and features of the invention are realized and attained by means of the instrumentalities, procedures and combinations particularly pointed out in the appended claims.

DETAILED DESCRIPTION

Figure 1A:
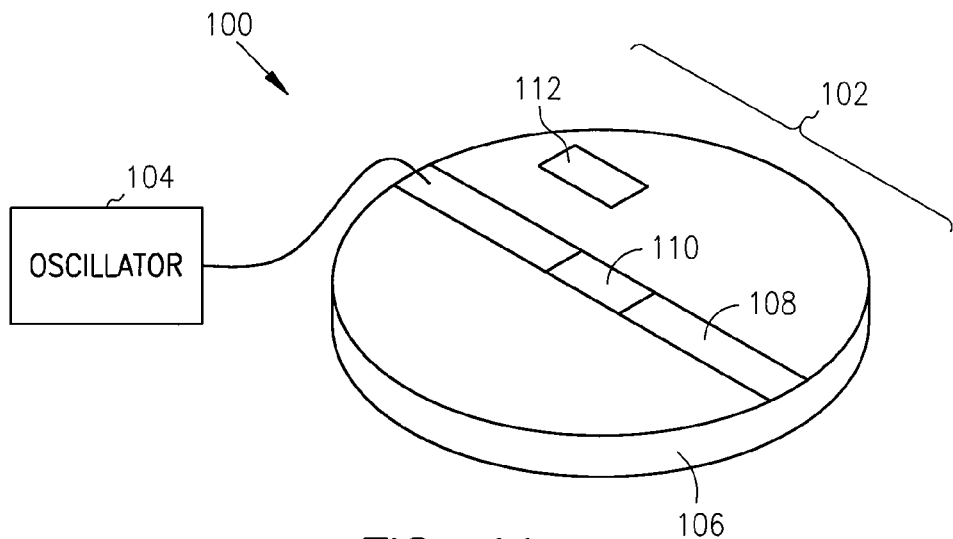
FIG. 1A is an illustration of a measurement system including a staging unit and an oscillator in accordance with one embodiment of the present invention.

In the following detailed description of the invention, reference is made to the accompanying drawings which form a part hereof, and in which are shown, by way of illustration, specific embodiments of the invention which may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. The following detailed description is not to be taken in a limiting sense, and the scope of the present invention is defined only by the appended claims, along with the full scope of equivalents to which such claims are entitled.

FIG. 1A is an illustration of a measurement system 100 including a staging unit 102 and an oscillator 104 in accordance with one embodiment of the present invention. The staging unit 102 includes a substrate 106 and a conductive electrode 108 formed on the substrate 106. The oscillator 104 is coupled to the conductive electrode 108. The substrate 106 includes a material having piezoelectric properties and a resonant frequency that varies with the mass of a sample (shown in FIG. 5 below) attached to an area 110 of the conductive electrode 108 or an area 112 of the substrate 106. The area 110 of the conductive electrode 108 and the area 112 of the substrate 106 are adapted (as described below) to receive the sample. The substrate 106 is not limited to being formed from a particular piezoelectric material. Any material which when mechanically stressed is capable of generating a polarization vector or charges on surfaces of the material or when strained develops an internal field and exhibits a voltage difference between surfaces is suitable for use in connection with the fabrication of the substrate 106. Exemplary piezoelectric materials suitable for use in connection with the measurement system 100 include quartz crystals, ceramics and salts. The substrate 106 is not limited to having a particular shape. In one embodiment the substrate 106 is substantially circular. The substrate 106 is also not limited to a substrate having a particular resonant frequency. Any resonant frequency capable of being processed in a signal processing system is suitable for use in connection with the measurement system 100. One exemplary resonant frequency is ten kilohertz.

The conductive electrode 108 is formed on the substrate 106 and, in operation, receives a signal from the oscillator 104. Any conductive material can be used in the fabrication of the conductive electrode 108. One exemplary class of materials suitable for use in the fabrication of the conductive electrode 108 includes metals. Exemplary metals suitable for use in the fabrication of the conductive electrode 108 include alloys of gold, silver, copper and platinum. A second exemplary class of materials suitable for use in the fabrication of the conductive electrode 108 includes non-metallic materials, such as polysilicon. Exemplary types of polysilicon suitable for use in the fabrication of the conductive electrode 108 include doped and undoped polysilicon. In one embodiment, the conductive electrode 108 forms a chord on the surface of the substrate 106. In an alternative embodiment, the conducive electrode 108 is aligned along a diameter of the substrate 106. The conductive electrode 108 is formed on the substrate 106 by sputtering or any other processes suitable for use in connection with the formation of conductive structures.

The oscillator 104 is an electronic circuit that is adapted to generate one or more signals of a substantially stable, fixed frequency. In one embodiment, the oscillator 104 is a variable oscillator and is adapted to generate a range of stable, fixed frequency signals including the resonant frequency of the substrate 106 when the substrate 106 is unloaded and the resonant frequency of the substrate 106 when the substrate 106 is loaded with a sample.

In operation, the measurement system 100 identifies the resonant frequency of the substrate 106 when the substrate 106 is unloaded, receives a sample (soft tissue including but not limited to cartilage, muscle and skin, gel-like material, or other material having a mass of about one microgram or less), generates the resonant frequency of the substrate 106 loaded with the sample and calculates the mass of the sample. In one embodiment, the mass is calculated using the Sauerbrey equation, which states that the change in the resonant frequency of the substrate 106 is directly proportional to the change in mass of the attached sample.

Figure 1B:
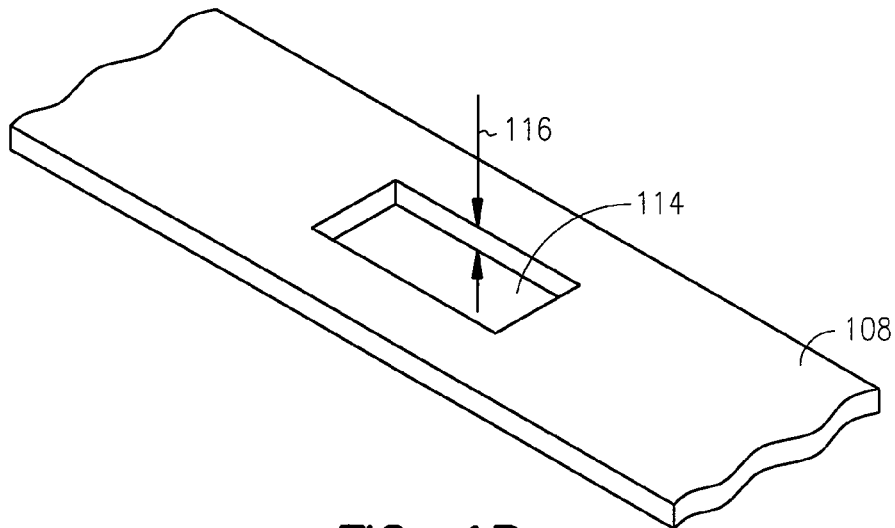
FIG. 1B is an illustration of a conductive electrode included in the staging unit shown in FIG. 1A and adapted to receive a sample in accordance with an alternative embodiment of the present invention.

FIG. 1B is an illustration of the conductive electrode 108 included in the staging unit 102 shown in FIG. 1A and adapted to receive a sample in accordance with an alternative embodiment of the present invention. The conductive electrode 108 is adapted to receive a sample by forming a recess 114 in the surface of the conductive electrode 108. The recess 114 has a depth 116 suitable for receiving a sliced tissue sample or a substantially liquid sample. For receiving a sliced tissue sample, the depth 116 is between about two microns and about ten microns. For receiving a substantially liquid sample, the depth 116 is about equal to the diameter of a single cell. A liquid sample can include a suspension of single cells. In one embodiment, the recess 114 has a substantially rectangular outer shape and is suitable for receiving a sliced tissue sample or a substantially liquid sample. However, the recess 114 is not limited to a particular outer shape. Recesses having substantially circular, square or triangular outer shapes are also suitable for use in connection with the adaptation of the conductive electrode 108. The shape of the recess 114 is selected to facilitate quick and accurate mounting of samples. Samples acquired by different methods often have different shapes, so the shape of the recess 114 is selected to correspond to the sample shape. Quick mounting of these samples is especially important for samples that degrade with time. Exemplary recesses suitable for use in connection with the adaptation of the conductive electrode 108 include cavities, depressions, and trenches. A cavity is a hollowed-out space in the conductive electrode 108. A depression is a low space, which is not necessarily hollowed out, in the conductive electrode 108. A trench is a narrow steep-sided depression in the conductive electrode 108. A particular type of recess is selected for use in connection with the measurement system 100 to facilitate the mounting of a particular type of sample on the conductive electrode 108.

In some embodiments, a material (not shown), such as a "biocompatible polymer" is formed on the conductive electrode 108 to improve adhesion between the electrode 108 and a sample. As used herein, the term "biocompatible polymer" refers to polymers that are well tolerated by the body and which do not cause a prolonged adverse inflammatory reaction or tissue necrosis that would affect their function or performance. These include materials which have little or no toxic or injurious effects on biological functions. The biocompatible polymers include natural or synthetic polymers, such as, for example, polyethylene glycol, polyvinyl alcohol, polyvinyl pyrrolidone, hyaluronic acid, collagen, poly(alpha esters) such as poly(lactate acid), poly(glycolic acid), polyorthoesters and polyanhydrides and their copolymers, which degraded by hydrolysis at a controlled rate and are reabsorbed. These materials provide the maximum control of degradability, manageability, size and configuration. Biocompatible polymer materials include polyglycolic acid and polygalactin, developed as absorbable synthetic suture material. Polyglycolic acid and polygalactin fibers may be used as supplied by the manufacturer. Other biocompatible materials include cellulose ether, cellulose, cellulosic ester, fluorinated polyethylene, phenolicpolymer, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinylidene fluoride, regenerated cellulose, silicone, urea-formaldehyde, or copolymers or physical blends of these materials. The material may be impregnated with suitable antimicrobial agents and may be colored by a color additive to improve visibility.

Figure 1C:
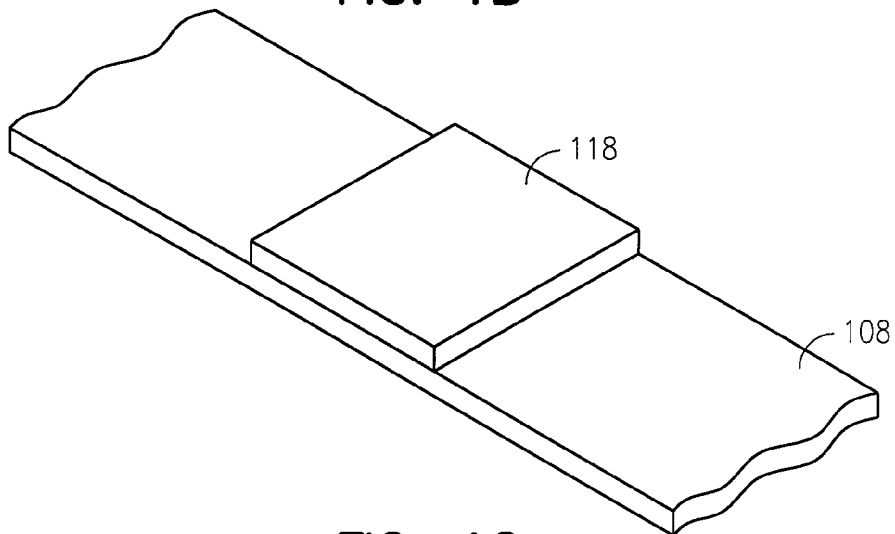
FIG. 1C is an illustration of a conductive electrode included in the staging unit shown in FIG. 1A and adapted to receive a sample in accordance with another alternative embodiment of the present invention.

FIG. 1C is an illustration of the conductive electrode 108 included in the staging unit 102 shown in FIG. 1A and adapted to receive a sample in accordance with another alternative embodiment of the present invention. A monolayer comprises one or more atomic layers. The conductive electrode 108 is adapted to receive a sample by forming a monolayer 118 on the conductive electrode 108. The material of the monolayer 118 is selected to bond to the conductive electrode 108 and to provide a bonding surface for a sample. Hydrophobic and hydrophilic materials are suitable for use in connection with the formation of the monolayer 118. The methods of mounting samples on the conductive electrode 108 shown in FIG. 1B and 1C are applicable to mounting samples in the area 112 (shown in FIG. 1A) of the substrate 106 (shown in FIG. 1A).

Figure 2A:
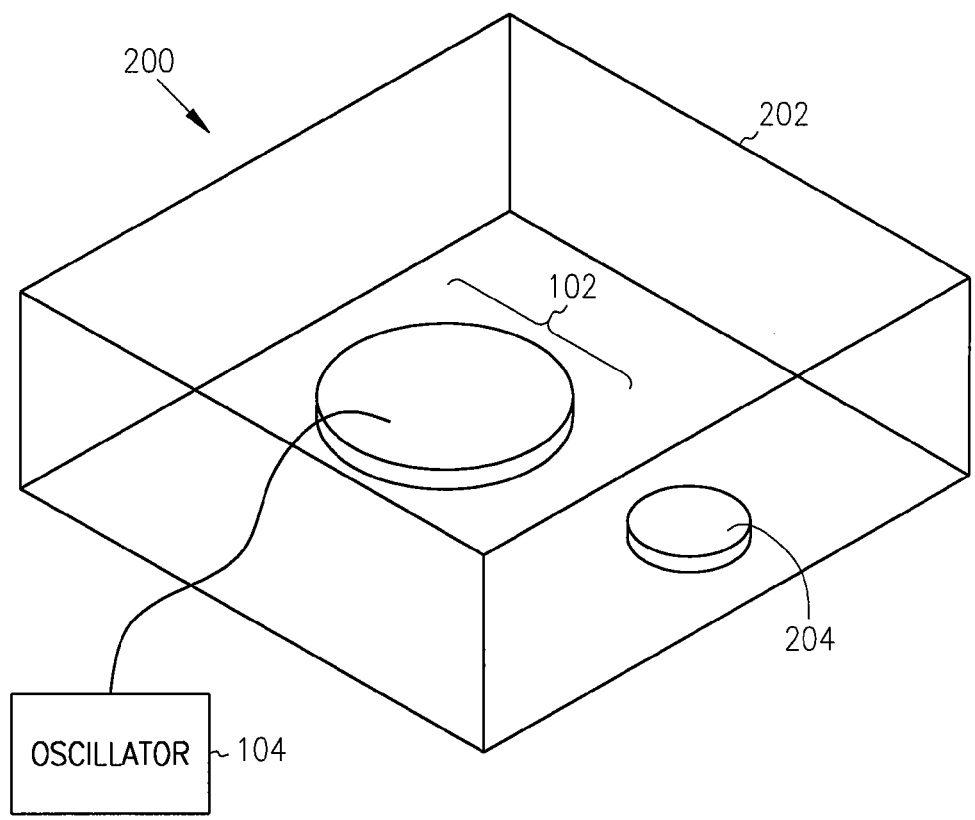
FIG. 2A is an illustration of a measurement system including an enclosure, a staging unit and a variable oscillator in accordance with yet another alternative embodiment of the present invention.

FIG. 2A is an illustration of a measurement system 200 including an enclosure 202, the staging unit 102 and the oscillator 104 in accordance with yet another alternative embodiment of the present invention. Although the embodiment shown in FIG. 2A only shows one staging unit, those skilled in the art will appreciate that multiple staging units, and thus multiple samples can be mounted and processed in the enclosure 202 of the measurment system 200. The enclosure 202 is shown in FIG. 2A as being transparent only to facilitate illustration of the staging unit 102 mounted (mounting not shown) within the measurement system 200. Thus, the enclosure 202 is not limited to being formed from a transparent material. Any material suitable for use in forming an enclosure is suitable for forming the enclosure 202. The enclosure 202 provides an environment in which the humidity is controllable. In other embodiments, vapor pressure, humidity, and temperature can be controlled. The humidity level in the enclosure 202 affects the amount of swelling (change in mass) in a particular sample. One method of controlling the humidity includes providing a solution 204, such as a salt solution, within the enclosure. In one embodiment, the concentration of the salt in the solution determines the relative humidity of the environment. Although the solution 204, in the embodiment shown in FIG. 2A, is shown in a container separate from the enclosure 202, in another alternative embodiment, the solution 204 covers the bottom surface of the enclosure 202. In one embodiment, the enclosure 202 is substantially sealed to assist in controlling the humidity in the enclosure 202. The oscillator 104 in FIG. 2A is coupled (as shown in FIG. 1A) to the conductive electrode 108 (shown in FIG. 1A) of the substrate 106 (shown in FIG. 1A) of the staging unit 102 (shown in FIG. 1A and FIG. 2A). The oscillator 104 is adapted to generate a range of frequencies that includes one or more resonant frequencies of the substrate.

It is appreciated that those of skill in the art understand that the solution 204 can include any suitable substance that effectively changes the vapor pressure of the solution. Suitable substances include, e.g., salts, polymers, small molecules, polyhydroxy organic molecules, carbohydrates, sugars, and surfactants. The substance will preferably be at least partially soluble in water and/or toluene. As used herein, "salt" refers to a product formed from the reaction of an acid with a base. As used herein, "polymer" refers to a high molecular weight substance that consists of many monomeric units. As used herein, "small molecule" refers to a substance that has a relatively low molecular weight (e.g., less than 2,000) with no repeating monomeric units. As used herein, a "polyhydroxy organic molecule" refers to a cyclic or alicyclic, branched or unbranched organic molecule that includes two or more hydroxyl (OH) groups. As used herein, "carbohydrate" or "sugar" refers to a ketonic or aldehydic derivative of higher polyalcohols. As used herein, a "surfactant" is a substance that even though present in relatively small amounts, can exert a marked effect on the surface behavior of a system. These agents are essentially responsible for producing changes in the surface energy of liquid or solid surfaces, and their ability to cause these changes in the surface energy of liquid or solid surfaces is associated with their tendency to migrate to the interface between two phases. Concise Encyclopedia of Science & Technology (McGraw-Hill) 4th Ed., 1998, 1931-1932. More specifically, the surfactant functions as an adjuvant to increase detergency and/or lubricity of the composition.

Suitable salts include, e.g., sodium chloride, potassium chloride, sodium sulfate, ammonium chloride and ammonium sulfate. Additional suitable salts are disclosed and commercially available from Aldrich Chemical Handbook (Milwaukee, Wis.).

The polymer can be, e.g., a block polymer, a branched polymer, a capped polymer, a graft polymer, or a homo polymer. See, e.g., Concise Chemical Dictionary, 4th edition, Chemical Publishing Company, New York, N.Y. (1986). The polymer can have any suitable molecular weight. Specifically, the polymer can have a molecular weight of up to about 1,000,000 g/mol. More specifically, the polymer can have a molecular weight of up to about 500,000 g/mol or up to about 100,000 g/mol. More specifically, the polymer can have a molecular weight of about 1,000 g/mol to about 100,000 g/mol.

The small molecule can have any suitable molecular weight. Specifically, the small molecule can have a molecular weight of less than to about 2,000 g/mol. More specifically, the small molecule can have a molecular weight of less than about 500 g/mol. More specifically, the small molecule can have a molecular weight of about 50 g/mol to about 750 g/mol.

Suitable sugars or carbohydrates include, e.g., sucrose, fructose, glucose, glucofuranose, mannose, idose, guloise, talose, galactose, altrose, allose, xylose, arabinose, and ribose. Additional suitable sugars or carbohydrates are disclosed and commercially available from Aldrich Chemical Handbook (Milwaukee, Wis.).

Suitable polyhydroxy organic molecules include, e.g., glycerol.

The surfactant can be an anionic surfactant, a cationic surfactant, a nonionic surfactant, an amphoteric surfactant, or any combination thereof. The surfactant composition can preferably include an anionic surfactant, wherein the anionic surfactant can preferably be a phosphate ester. The surfactant composition can also preferably include a cationic surfactant, wherein the cationic surfactant can preferably be a quaternary ammonium salt. The surfactant composition can also preferably include a nonionic surfactant, wherein the nonionic surfactant can preferably be an alcohol alkoxylate (e.g., ethoxylate). In addition, the surfactant composition can also preferably include a amphoteric surfactant, wherein the amphoteric surfactant can preferably be a fatty amine derivative.

As used herein, an "anionic surfactant" is a compound containing a hydrophobic hydrocarbon moiety and a negatively charged hydrophilic moiety. Typical commercially available anionic surfactants provide either a carboxylate, sulfonate, sulfate, or phosphate group as the negatively charged hydrophilic moiety. Any commercially available anionic surfactant may be employed in the composition of the invention. Suitable exemplary anionic surfactants include, e.g., phosphate esters, alkyl sulfates, alkyl sulfonates, aromatic sulfonates, alpha-olephin sulfonates, and ether carboxylates.

As used herein, a "cationic surfactant" is a compound carrying a positive charge on the surfactants's hydrophilic portion. Usually the positive charge is on a nitrogen atom in the form of a quaternary ammonium compound, an amine salt, or an imidazoline salt. Suitable exemplary cationic surfactants include, e.g., quaternary ammoniums, amines, diamines, and amine oxides. Suitable exemplary cationic surfactants include, e.g., quaternary ammoniums, amines, diamines, and amine oxides.

As used herein, an "nonionic surfactant" is a hydrophobic compound that bears essentially no charge and exhibits a hydrophilic tendency usually due to the presence of oxygen in the molecule. Nonionic surfactants encompass a wide variety of polymeric compounds which include specifically, but not exclusively, alkoxylated (e.g., ethoxylated) alkylphenols, alkoxylated (e.g., ethoxylated) aliphatic alcohols, alkoxylated (e.g., ethoxylated) amines, alkoxylated (e.g., ethoxylated) ether amines, carboxylic esters, carboxylic amides, and polyoxyalkylene oxide block copolymers. Any desired nonionic surfactant can be employed in the composition of the invention.

As used herein, an "amphoteric surfactant" is a compound that includes both an acidic and a basic hydrophilic group. Amphoteric surfactants can include the anionic or cationic group common in anionic or cationic surfactants and additionally can include either hydroxyl or other hydrophilic groups that enhance surfactant properties. Suitable amphoteric surfactants include betaine surfactants, sulfobetaine surfactants, amphoteric imidazolinium derivatives, sarcosinates, and amino acid derivatives.

Figure 2B:
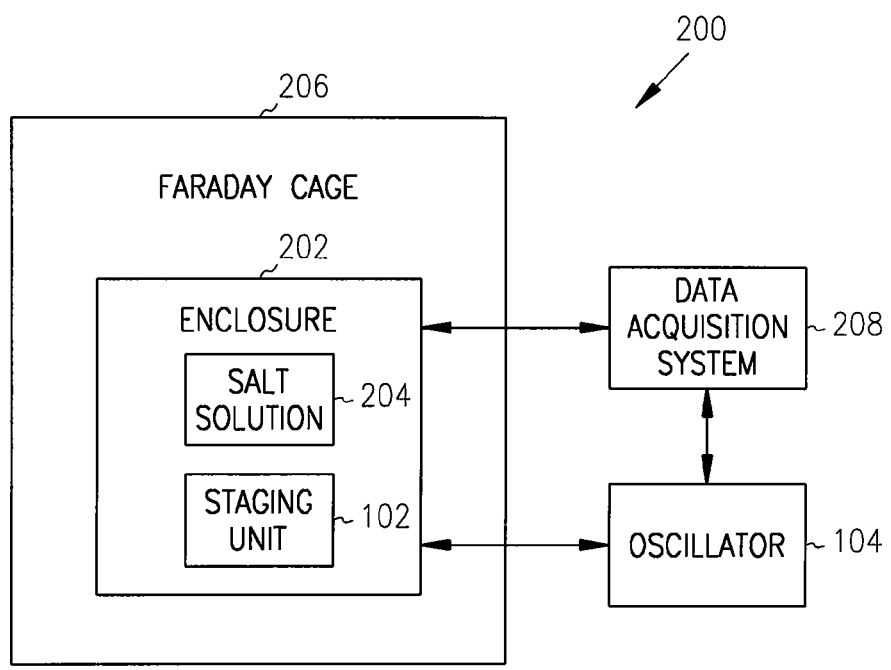
FIG. 2B is a block diagram of the measurement system shown in FIG. 2A including a Faraday cage and a data acquisition system in accordance with still another alternative embodiment of the present invention.

FIG. 2B is a block diagram of the measurement system 200 shown in FIG. 2A including a Faraday cage 206 and a data acquisition system 208 in accordance with still another alternative embodiment of the present invention. The enclosure 202 is mounted within the Faraday cage 206 to provide electromagnetic shielding for the enclosure 202. In operation, the data acquisition system 208 controls the temperature and the humidity level in the enclosure 202 and the output of the oscillator 104.

Figure 3:
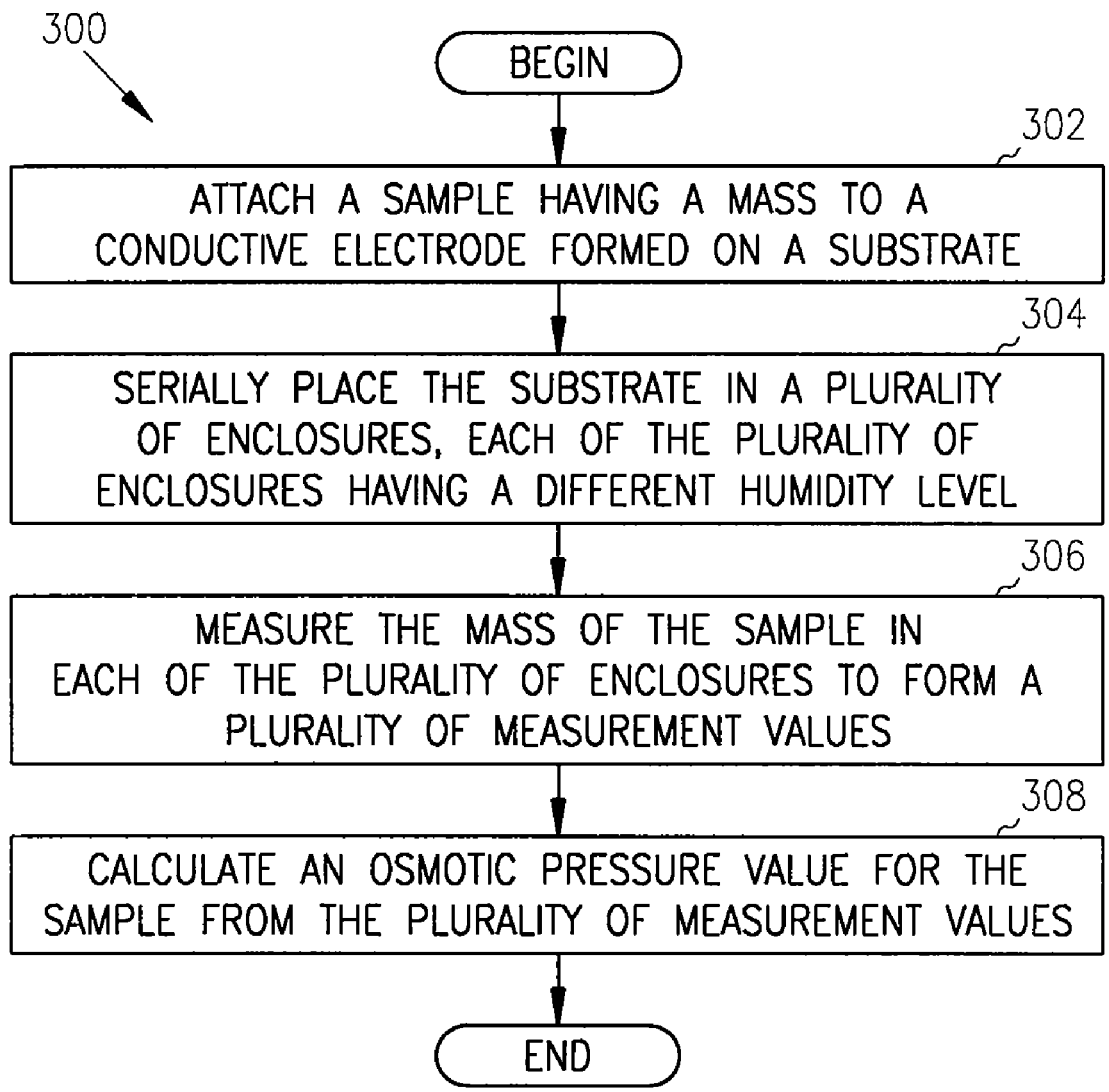
FIG. 3 is a flow diagram of a method of measurement in accordance with one embodiment of the present invention.

FIG. 3 is a flow diagram of a method 300 of measurement in accordance with one embodiment of the invention. The method 300 includes attaching a sample having a mass to a conductive electrode formed on a substrate (block 302), serially placing the substrate in a plurality of enclosures, each of the plurality of enclosures having a different humidity level (block 304), measuring the mass of the sample in each of the plurality of enclosures to form a plurality of measurement values (block 306) and calculating an osmotic pressure value (the hydrostatic pressure at which the flow of a solvent through a membrane stops) for the sample from the plurality of measurement values (block 308).

Figure 4:
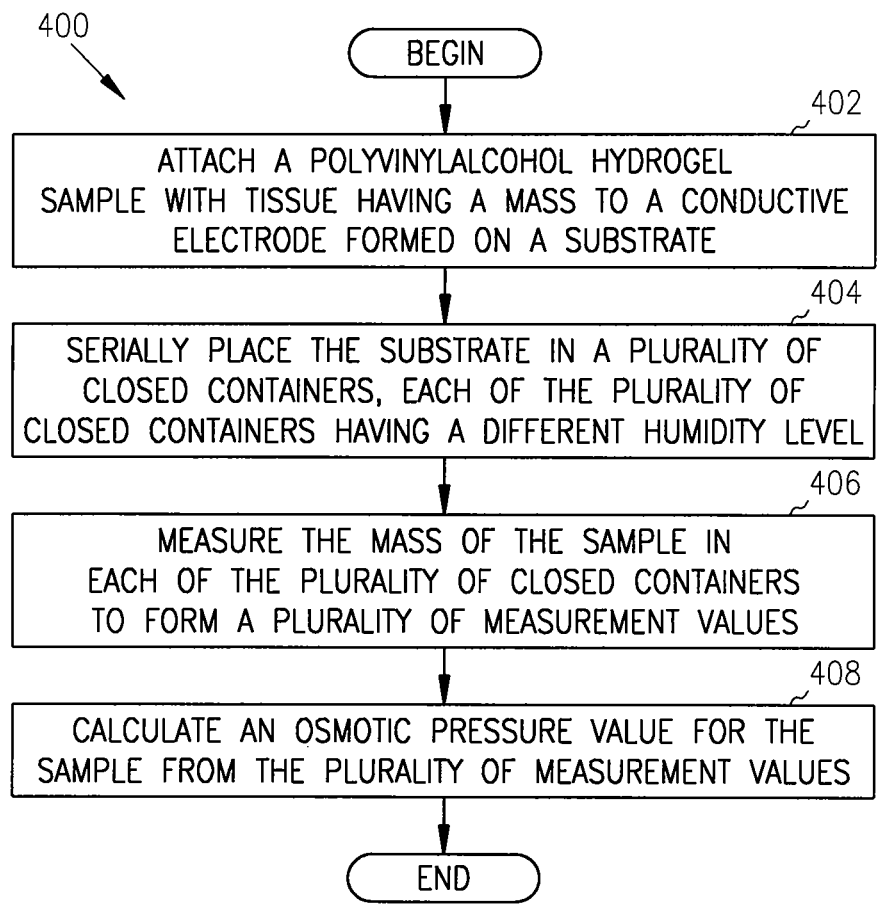
FIG. 4 is a flow diagram of a method of measurement in accordance with an alternative embodiment of the present invention.

FIG. 4 is a flow diagram of a method 400 of measurement in accordance with an alternative embodiment of the present invention. The method 400 includes attaching a polyvinylalcohol hydrogel sample with tissue having a mass to a conductive electrode formed on a substrate (block 402), serially placing the substrate in a plurality of closed containers, each of the plurality of closed containers having a different humidity level (block 404), measuring the mass of the sample in each of the plurality of closed containers to form a plurality of measurement values (block 406) and calculating an osmotic pressure value for the sample from the plurality of measurement values (block 408).

Figure 5:
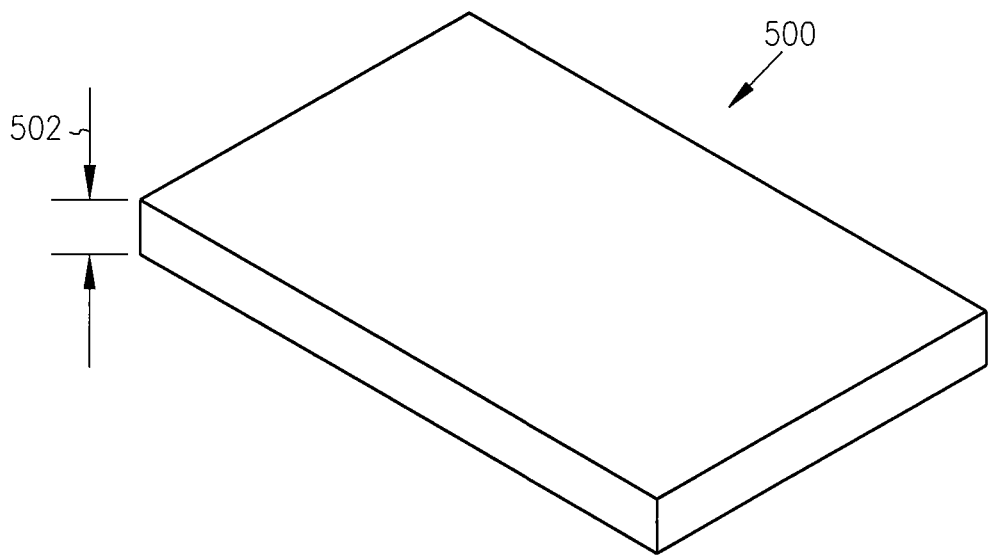
FIG. 5 is an illustration of a tissue sample having a thickness of between about 0.2 microns and about 500 microns suitable for use in connection with some embodiments of the present invention.

FIG. 5 is an illustration of a tissue sample 500 having a thickness 502 of between about 0.2 microns and about 500 microns suitable for use in connection with some embodiments of the present invention. The thickness 502 can vary with the method of preparation of the tissue sample 500 and the types of cells included in the sample. The tissue sample 500 includes a collection of cells and can be generated by a variety of methods. For example, the tissue sample 500 can be generated by slicing tissue from a subject, such as in a biopsy operation, or by creating a suspension of cells. The thickness 502 of suspensions of cells on the substrate 106 (shown in FIG. 1A) or the conductive electrode 108 (shown in FIG. 1A) can approach the thickness of a single cell. For example, for cell suspensions of *e. coli* bacterium cells, the thickness 502 of the suspension can be as thin as about 2 microns. For cell suspensions of animal cells, the thickness 502 of the suspension can be between about 10 microns and about 20 microns. For cell suspensions of cartilage samples, the thickness 502 of the suspension can be between about 10 microns and about 20 microns. For cell suspensions of plant cells, the thickness 502 of the suspension can be between about 30 microns and about 50 microns. And for cell suspensions of prokaryotic cells, the thickness 502 of the suspension can be between about 0.2 microns and about 500 microns.

The embodiments of the methods and systems described provide rapid measurements of small physical changes in one or more samples, including samples having only small amounts of material, such as micro-grams of material, and samples having overlapping molecules. Exemplary applications of the methods and systems described include identification of diseased or damaged tissue samples, including tissue samples that exhibit high osmotic pressures (pressures greater than about 1000 Pascals), rigid tissue, such as bone, and the measurement of small changes in the mass of non-biological samples.

Although specific embodiments have been described and illustrated herein, it will be appreciated by those skilled in the art, having the benefit of the present disclosure, that any arrangement which is intended to achieve the same purpose may be substituted for a specific embodiment shown. This application is intended to cover any adaptations or variations of the present invention. Therefore, it is intended that this invention be limited only by the claims and the equivalents thereof.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention

What is claimed is:

1. A method comprising:
    attaching a sample having a mass to a conductive electrode formed on a substrate;
    serially placing the substrate in a plurality of enclosures, each of the plurality of enclosures having a different humidity level; and
    measuring the mass of the sample in each of the plurality of enclosures to form a plurality of measurement values.

2. The method of claim 1, further comprising calculating an osmotic pressure value for the sample from the plurality of measurement values.

3. The method of claim 2, wherein measuring the mass of the sample in each of the plurality of enclosures comprises:
    identifying a frequency at which the substrate is resonant.

4. The method of claim 3, wherein identifying the frequency at which the substrate is resonant comprises:
    applying one or more signals of different frequencies to the conductive electrode; and
    identifying one of the one or more frequencies as a resonant frequency.

5. The method of claim 1, wherein attaching the sample having the mass to the conductive electrode comprises:
    forming a monolayer on the conductive electrode; and
    forming the sample on the monolayer.

6. The method of claim 5, wherein forming the monolayer on the conductive electrode comprises:
    forming a monolayer of a hydrophobic material on the conductive electrode.

7. The method of claim 5, wherein forming the monolayer on the conductive electrode comprises:
    forming a monolayer of a hydrophilic material on the conductive electrode.

* * * * *